United States Patent [19]

Nakano

[11] Patent Number: 5,581,821
[45] Date of Patent: Dec. 10, 1996

[54] REELABLE EAR PLUGS FOR CONSTRUCTION HELMETS

[76] Inventor: Steven A. Nakano, 1009 Millmark Grove, San Pedro, Calif. 90731

[21] Appl. No.: 494,346

[22] Filed: Jun. 26, 1995

[51] Int. Cl.⁶ .................................................. A42B 3/16
[52] U.S. Cl. ........................ 2/422; 2/209.13; 2/423; 128/866; 181/135; 242/385.1; 242/385.3
[58] Field of Search ............................. 2/422, 423, 209, 2/2, 1, 209.13; 128/864, 866; 181/130, 135; 242/385.1, 385.3

[56] References Cited

U.S. PATENT DOCUMENTS

| | | | |
|---|---|---|---|
| D. 277,317 | 1/1985 | Eisenmenger | D24/67 |
| 3,021,090 | 2/1962 | Becker | 242/385.3 |
| 3,461,463 | 8/1969 | Beguin | 2/423 |
| 3,841,326 | 10/1974 | Leight | 2/423 |
| 3,970,082 | 7/1976 | Leight | 2/423 |
| 4,384,688 | 5/1983 | Smith | 242/385.1 |
| 4,957,248 | 9/1990 | Schmidt | 242/385.3 |
| 4,989,805 | 2/1991 | Burke | 242/385.1 |
| 5,074,375 | 12/1991 | Grozil | 181/135 |
| 5,094,396 | 3/1992 | Burke | 242/385.1 |
| 5,193,226 | 3/1993 | Mortenson | 2/422 |
| 5,438,698 | 8/1995 | Burton et al. | 2/209.13 |

*Primary Examiner*—Michael A. Neas
*Attorney, Agent, or Firm*—Roger A. Marrs

[57] ABSTRACT

A construction helmet is disclosed having a housing detachably mounted thereon which supports a ratcheted take-up reel having a pair of ear plugs attached to a hub by flexible cords wound about the hub. The reel is rotatably carried on the housing and a manually operable plunger releases the reel for automatic withdrawal of the ear plugs into a storage receptacle on the housing. Strain relief elements are attached to each cord and the receptacle includes shoulder straps engageable with the strain relief elements. The plunger is releasably connected to ratchet teeth carried on the reel hub.

6 Claims, 2 Drawing Sheets

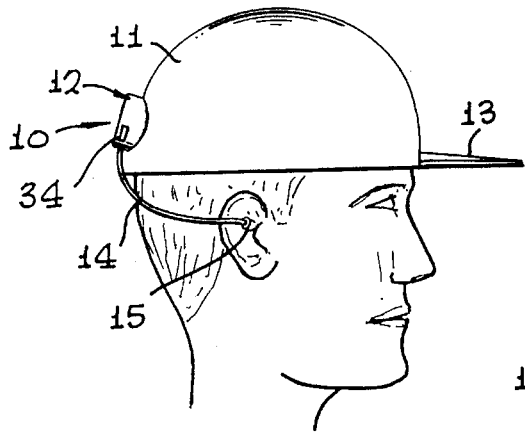
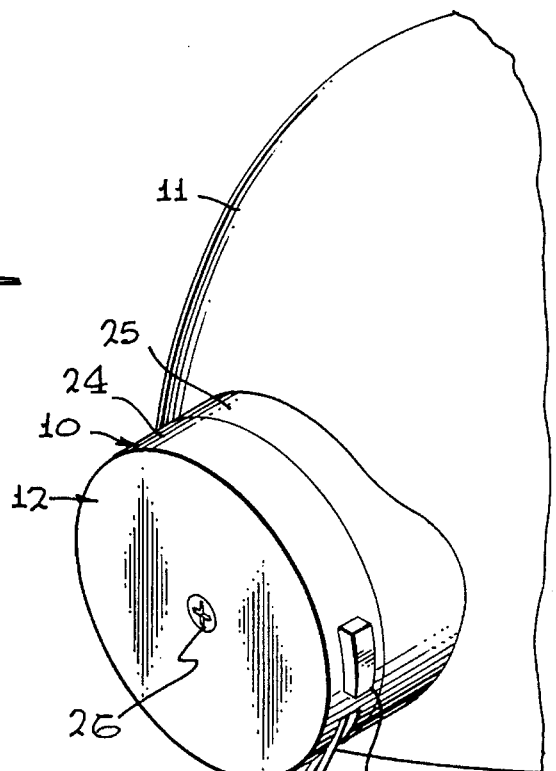
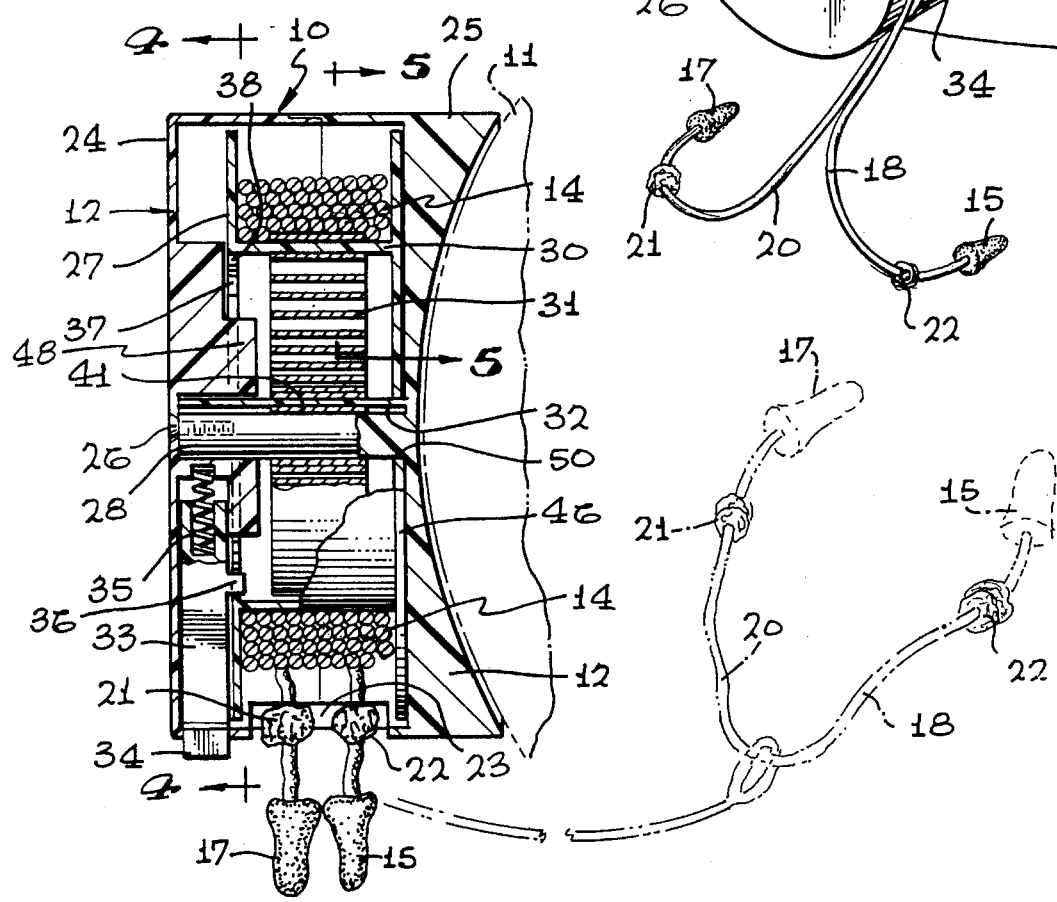

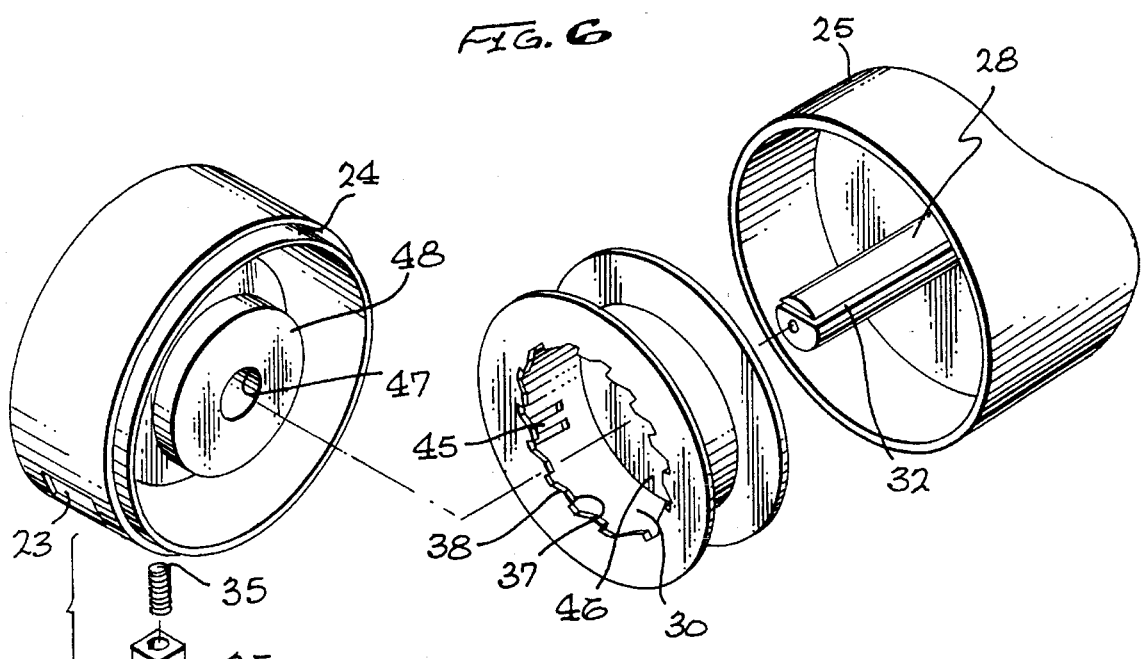
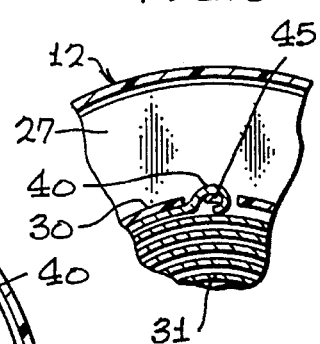
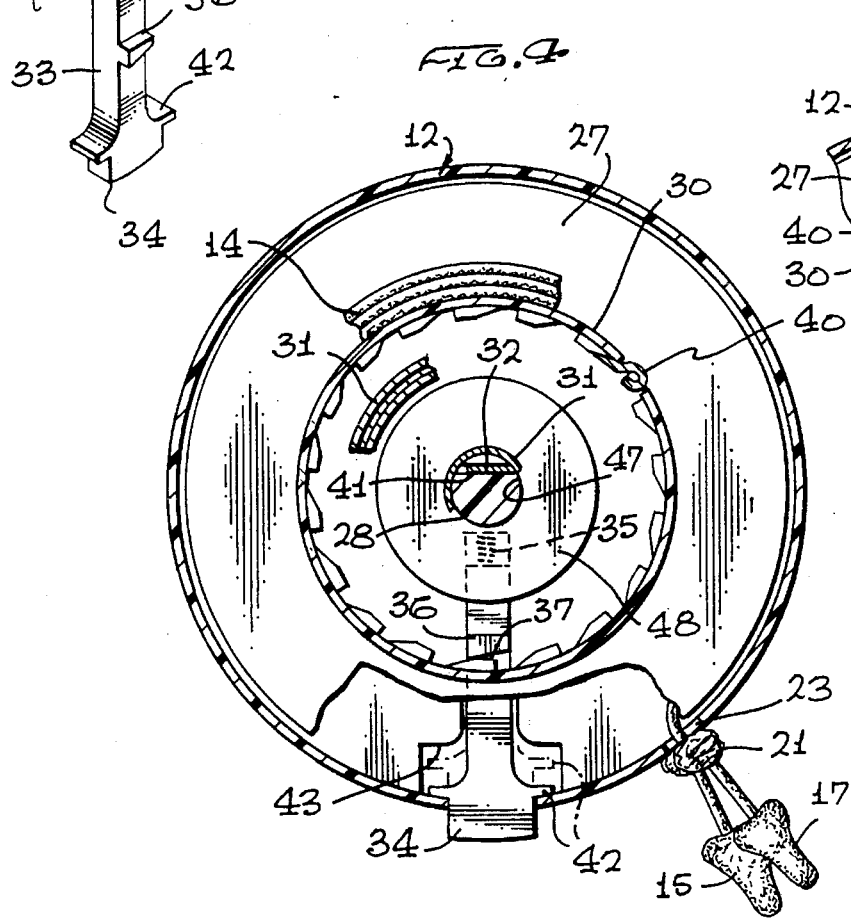

5,581,821

1
REELABLE EAR PLUGS FOR CONSTRUCTION HELMETS

BACKGROUND OF THE INVENTION

1. Field of the Invention

The present invention relates to the field of ear protector assemblies, and more particularly to a novel ear plug assembly which may be detachably carried on a construction helmet that includes automatic retraction of the ear plugs onto a storage reel under control of a biasing spring in response to manual plunger or switch action.

2. Brief Description of the Prior Art

In the past, it has been the conventional practice to use ear plugs in order to protect the ears of workmen while on the job. Workmen who must wear protective helmets or hardhats to protect against falling objects or the like must occasionally work around noisy machinery or be subjected to noisy environmental conditions. In order to store the ear plugs or protectors in a convenient location for the workmen, a variety of attempts have been made to provide elastic band arrangements, storage boxes or the like in order to conveniently provide the ear plugs for the workmen while on a job site. Some attempts are disclosed in U.S. Pat. Nos. 3,841,326; 3,461,463 and 5,074,375. Although some of these devices have been operable for their intended purposes, problems and difficulties have been encountered which stem largely from the fact that although the ear plugs may be tethered to a housing, no means is disclosed for coiling or storing the cord and the ear plugs in a convenient manner when not in use. Nor does the prior art disclose a detachable connection of any housing with a construction helmet.

Therefore, a long-standing need has existed to provide a novel means having ear plugs connected by cords to a reelable device wherein the device is detachably or releasably connected to the brim or crown of a construction helmet so that the ear plugs are convenient for use. Such reelable ear plugs should further include a means for automatically coiling or storing the cord for the ear plugs in a convenient manner, such as by employing a negator or coil spring or the like in combination with a ratcheted reel which is under the control of a finger-operated plunger or release mechanism.

SUMMARY OF THE INVENTION

Accordingly, the above problems and difficulties are avoided by the present invention which provides a novel reelable ear plug assembly having a housing which is detachably connected to a construction helmet wherein the housing rotatably supports a reel for storing a quantity of cord about a central hub. One end of the cord is fixed to the hub while the opposite end is bifurcated to support a pair of ear plugs. A coil spring is operably coupled between the hub and the housing so as to automatically cause the reel to turn in a winding direction withdrawing the cord and ear plugs to the housing for storage. A control mechanism taking the form of a spring-loaded plunger is manually operated on the housing in cooperation with ratchet teeth provided on the reel hub so that release of the reel is effected permitting automatic withdrawal of the cord and ear plugs to the housing.

Therefore, it is among the primary objects of the present invention to provide a novel ear plug assembly for conveniently mounting a pair of ear plugs including retaining or tethered cords onto a reelable mechanism carried on a housing.

2

Another object of the present invention is to provide a novel means for coiling a length of cord having a pair of ear plugs connected at one end so that the ear plugs may be conveniently carried on a construction helmet in a readily accessible manner for use by a workman.

Another object of the present invention is to provide a novel housing having a spring-loaded reel carried thereon which is used for storing a length of cord having ear plugs attached thereto and which includes a control means operably coupled between the reel and the housing for selectively permitting withdrawal of the cord and ear plugs to the housing.

Yet another object of the present invention is to provide a convenient means for withdrawing ear plugs and their attendant cord into a spring-loaded reel carried on a housing in response to a spring-loaded plunger mechanism operable in cooperation with ratchet teeth carried on a reel.

A further object resides in providing an end loop for slidably holding a second cord having the ear-plugs fastened to its opposite ends so that replacement is easily achieved.

BRIEF DESCRIPTION OF THE DRAWINGS

The features of the present invention which are believed to be novel are set forth with particularity in the appended claims. The present invention, both as to its organization and manner of operation, together with further objects and advantages thereof, may best be understood with reference to the following description, taken in connection with the accompanying drawings in which:

FIG. 1 is a side elevational view of a construction helmet having the detachable ear plug assembly connected thereto;

FIG. 2 is an enlarged rear perspective view of the helmet shown in FIG. 1 illustrating the ear plug assembly incorporating the present invention;

FIG. 3 is an enlarged transverse cross-sectional view of the ear plug assembly shown in FIG. 2;

FIG. 4 is a cross-sectional view of the ear plug assembly shown in FIG. 3 as taken in the direction of arrows 4—4 thereof;

FIG. 5 is a fragmentary sectional view of the housing and reel of the ear plug assembly illustrating the connection of the coiled spring for retraction purposes;

FIG. 6 is a perspective exploded view showing the major components of the ear plug assembly illustrated in FIGS. 1–4 inclusive.

DESCRIPTION OF THE PREFERRED EMBODIMENT

Referring to FIG. 1, the novel ear plug assembly of the present invention is illustrated in the general direction of arrow 10 which includes a reelable ear plug assembly detachably carried on a helmet 11, such as is used by a construction worker. The helmet may be referred to as a construction helmet and the assembly is carried on a housing 12 which may be attached to the rear of the helmet, as shown, such as with adhesive or by a releasable clamp, or, if desired, the housing may be detachably connected to a brim or visor 13 formed with the crown of the helmet 11. The housing 12 stores a length of cord 14 to which a pair of ear plugs, such as plug 15, may be attached. The cord 14 is bifurcated into a pair of cords with their terminating ends secured to the ear plugs. As illustrated, the cord 14 has been withdrawn from the housing 12 and the ear plugs are in position in the ears of the user for the user's protection. It can be seen that the housing is conveniently placed so that it will not interfere with the workman during the performance of his job and yet the ear plugs may readily be withdrawn from a storage position in the housing for use as illustrated. The withdrawing of the length of cord 14 is against the tension of a spring within the housing and when a control plunger or button 34 is actuated, the spring automatically retracts the cord and ear plugs to the housing 12.

Referring now in detail to FIG. 2, it can be seen that the ear plugs 15 and 17 are connected on the ends of cord segments 18 and 20 which, in turn, are connected to the single cord 14. The cord segments include strain relief elements 21 and 22 that seat against a shoulder within the receptacle 23 of the housing so as to stop further retraction. The ear plugs 15 and 17 will then dangle from the receptacle and the strain elements. When it is desired to retract the cord and the ear plugs, the plunger 34 is depressed which causes the internal spring to reel in the cord and ear plugs. The housing may be constructed in two halves, such as indicated by numerals 24 and 25, and the halves may be releasably held together by means of a fastener 26.

Referring now to FIG. 3, it can be seen that the cord 14 and the cord segments 18 and 20 are wound for storage on a reel 27 which is internally mounted within the housing 12 on a fixed shaft 28. It can be seen that the reel 24 includes a hub 30 on which the cord and cord segments are wound when in a storage condition. It can also be seen that a spring 31 is included which has one end connected to the hub 30 while its opposite end is connected to the fixed shaft 28 within a slot 32. A control mechanism is illustrated which takes the form of a plunger 33 having an exposed finger-depressing portion 34 which would operate against the expansion of a coil spring 35 to release a latch 36 from an engaged position with a selected one of a plurality of teeth 37 carried on the inner diameter of a flange 38 joined with the hub 30 and movable with the reel 27. Therefore, it can be seen that when the ear plugs 15 and 17 are withdrawn from the housing so that the cord is unwound from the reel, the unwinding takes place against the tension of spring 31. When the desired length of cord has been withdrawn, the reel has a tendency to wind back all of the cord except that the latch 36 will engage with a selected one of the teeth 37 on the flange 38. Unless the plunger 33 is depressed, the reel will not rewind the cord and the ear plugs will remain in an extended position such as shown in broken lines in FIG. 3.

Referring now in detail to FIG. 4, it can be seen that one end of the spring 31 which is commonly known as a negator or retractor spring is connected to the hub 30 via a hooked end 40. However, the opposite end of the retractor spring 31 is connected through a slot in the fixed shaft 28 and is represented by the numeral 41. Also, the latch 36 is shown adjacent to the tooth 37. When the latch is behind the tooth at its flat end, retention of the reel is in position with respect to the housing. However, each tooth is provided with a trailing ramp that slidably engages with a sloping surface on the latch 36 to permit unrestricted rotation of the reel in a given direction. A pair of flanges 42 placed on either side of the exposed plunger portion 34 engage with the underside of the housing to prevent the plunger from leaving its installed position on the housing. The plunger is permitted to move the flanges 42 within the confines of a receptacle 43 which maintains the plunger on the housing. The shaft of the plunger passes through an aperture and bears against the expansion spring 35. The spring 31 allows the reel to unwind when the reel turns in a clockwise direction. The spring 31 causes withdrawal of the ear plugs and the cord onto the reel when the reel is moved in its counterclockwise direction in response to the tightened tension of the retractor spring 31.

In FIG. 5, the connection of the retractor spring 31 is illustrated as connecting with the hub 30. Also, it can be seen that the reel 27 operates and rotates within the housing 12.

Referring now in detail to FIG. 6, it can be seen that the shaft 28 includes a slot 44 into which the spring end 41 is connected. The connection for the spring end 40 is through the slots and about a bar 45 carried on the hub 30 of the reel. The flange 38 with the plurality of teeth 37 is clearly illustrated and the latch 36 on the plunger 33 selectively engages with plurality of teeth 37. The shaft 28 supports the reel by means of a hole 50 in backing plate 46 in one-half of the housing and by the flat surfaces of each tooth resting on the adjacent surface of disc 48 on the other half of the housing. The shaft 28 extends into the hole 47. Thus, the reel is supported on the shaft 28 and the disc 48 and, therefore, the reel is permitted to rotate within the housing..

In view of the foregoing, it can be seen that the housing 12 may readily be attached to the crown of the helmet 11 and that the ear plugs 15 and 17 may readily be withdrawn from the housing for use by the workman. As the ear plugs are withdrawn, the cord is unwound from the reel and the spring 31 will tighten. The reel is prevented from rotating in a reverse direction by means of the plunger latch 36 catching with the flat front side of a selected one of the teeth 37. However, upon depression of the plunger 34, the latch 36 is removed from the tooth and the stored tension of the spring 31 causes the reel to rotate in the opposite direction to withdraw the cord and the ear plugs. The strain relief elements 21 and 22 bear against the shoulder edges of the receptacle 23 to stop further withdrawal of the cord or the ear plugs into the housing.

Since cord 18, 20 slides through a loop at the end of cord 14, replacement of the ear plugs is convenient and does not require disassembly or undoing of the components.

While particular embodiments of the present invention have been shown and described, it will be obvious to those skilled in the art that changes and modifications may be made without departing from this invention in its broader aspects and, therefore, the aim in the appended claims is to cover all such changes and modifications as fall within the true spirit and scope of this invention.

What is claimed is:

1. Reelable ear plug assembly comprising:

a housing;

a reel rotatably mounted internally in said housing;

a set of ear plugs;

cord means connecting said set of ear plugs to said reel;

a spring means operably disposed between said housing and said reel normally biasing said reel to withdraw said set of ear plugs towards said housing;

a manually operated plunger and latch means releasably coupled between said reel and said housing for selectively engaging and disengaging said reel from said housing;

said spring means includes a coil leaf spring having opposite end connected to said housing and said reel respectively;

headgear having a crown and a forwardly extending peak;

means for detachably mounting said housing to said headgear whereby said set of ear plugs are deployable for use on the sides of the user's head;

said plunger and latch means includes a ratchet mechanism having teeth carried on said reel and a latch element carried on said plunger of said means selectively engageable with said teeth; and said housing includes two halves with a shaft projecting from one half rotatably supporting said reel on one side and a disc carried on the other half rotatably supporting the other side of said reel.

2. The invention as defined in claim 1 wherein:

said cord means includes:

a single strand having two ends with one end fixed to said reel and the other end terminating with a closed loop;

a string passed through said loop having opposite ends secured to ear plugs respectively.

3. The invention as defined in claim 2 wherein:

said reel includes a hub separating a pair of side discs;

said teeth depending from one disc of said pair; and each tooth having a flat surface slidably engageable with said housing disc.

4. The invention as defined in claim 3 including:

said string having a strain relief nub and stop adjacent to each of said ear plugs.

5. The invention as defined in claim 4 wherein:

said housing is provided with an opening passing said cord from said reel to said set of ear plugs.

6. The invention as defined in claim 5 wherein:

said plunger and latch means is yieldably and resiliently biased out of engagement with said reel teeth.

* * * * *